United States Patent [19]

Gavin

[11] 3,960,963

[45] June 1, 1976

[54] SEPARATION OF 3,4-DIAMINOTOLUENE FROM A MIXTURE OF o-TOLUENEDIAMINE ISOMERS

[75] Inventor: David F. Gavin, Chesire, Conn.

[73] Assignee: Olin Corporation, New Haven, Conn.

[22] Filed: July 29, 1974

[21] Appl. No.: 492,648

Related U.S. Application Data

[63] Continuation of Ser. No. 417,008, Nov. 19, 1973, abandoned.

[52] U.S. Cl. .............................................. 260/582
[51] Int. Cl.² ........................................ C07C 85/26
[58] Field of Search .................................. 260/582

[56] References Cited

UNITED STATES PATENTS

| | | | |
|---|---|---|---|
| 2,623,903 | 12/1952 | Weaver et al. | 260/582 |
| 3,149,162 | 9/1964 | Gardner et al. | 260/582 |
| 3,203,994 | 8/1965 | Spiegler | 260/582 |
| 3,314,996 | 4/1967 | Luberoff et al. | 260/582 |
| 3,317,606 | 5/1967 | Luberoff et al. | 260/582 |

*Primary Examiner*—Paul F. Shaver
*Attorney, Agent, or Firm*—Robert L. Andersen

[57] ABSTRACT

Purified 3,4-toluenediamine is separated from a mixture of o-toluenediamine isomers containing principally 3,4-toluenediamine and 2,3-toluenediamine by crystallizing from a solvent selected from the group consisting of toluene, benzene and xylene.

5 Claims, 1 Drawing Figure

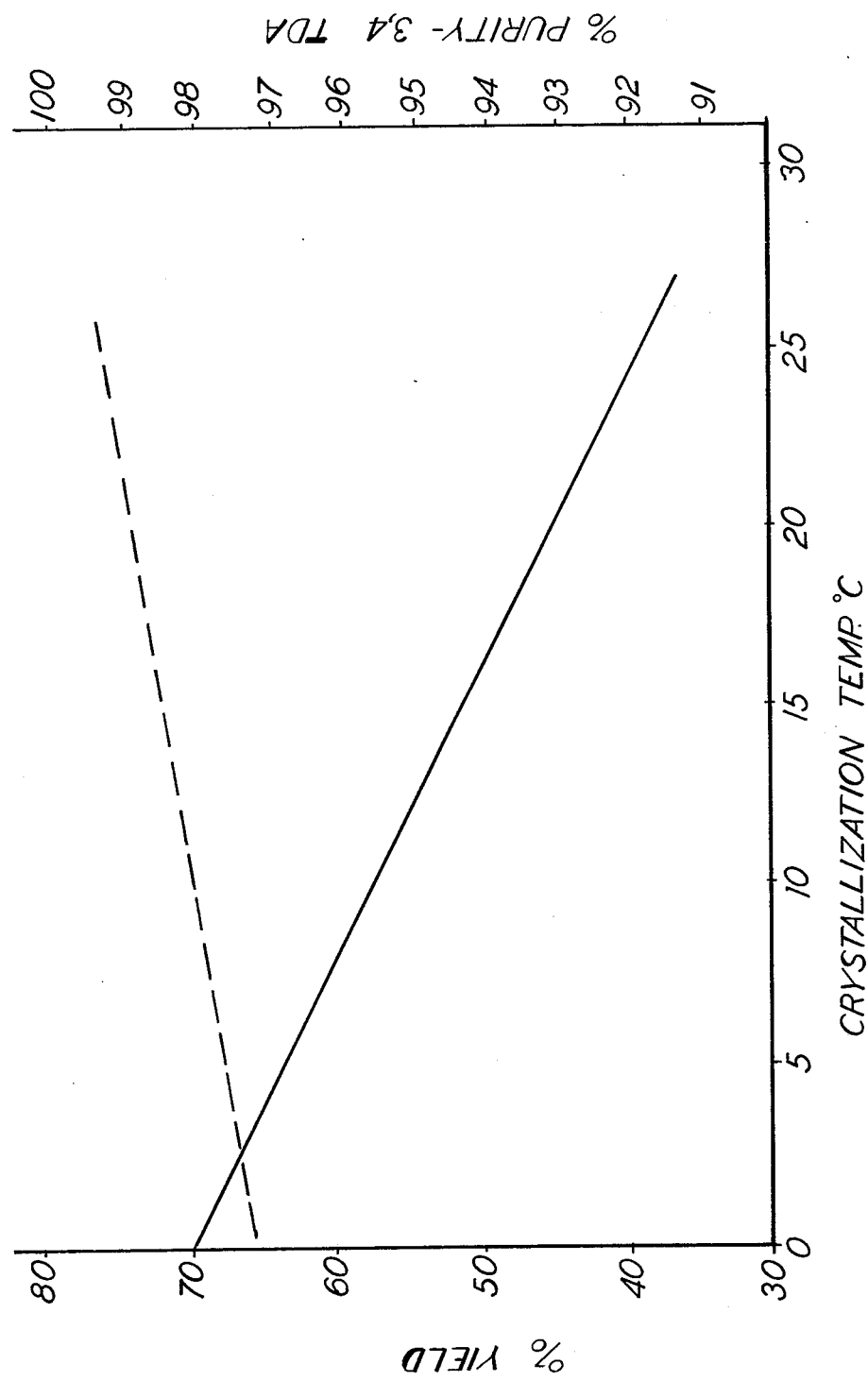

SEPARATION OF 3,4-DIAMINOTOLUENE FROM A MIXTURE OF O-TOLUENEDIAMINE ISOMERS

RELATED APPLICATION

This application is a continuation of application Ser. No. 417,008, filed Nov. 19, 1973, now abandoned.

BACKGROUND OF THE INVENTION

The present invention relates to the separation of 3,4-toluenediamine from a mixture containing 3,4- and 2,3-toluenediamine by selectively crystallizing from a solvent selected from the group consisting of toluene, xylene and benzene.

Toluene diisocyanate is a valuable intermediate in the preparation of polyurethanes. At present, about 500 million pounds are being consumed each year and it has been estimated that its use will increase to about 800 million pounds per year by the end of 1975.

Toluene diisocyanate is generally produced by dinitrating toluene to produce mixed dinitrotoluenes, reducing the mixed dinitrotoluenes to form a mixture of toluenediamines, separating from the desired 2,4- and 2,6-toluenediamine isomers a by-product fraction containing mixed o-toluenediamine isomers and converting the desired fraction to toluene diisocyanate by reaction with phosgene. The by-product fraction is generally separated by fractional distillation as disclosed in U.S. Pat. Nos. 3,149,162 and 3,637,514.

About 30 million pounds of the by-product fraction containing mixed o-toluenediamines is currently produced annually in the United States. A substantial amount of this is discarded. The remainder is put to uses where the mixed ortho isomers can be utilized without separation. An example of the use of the mixed ortho isomers is their conversion to mixed tolutriazoles for use as corrosion inhibitors in antifreezes and for use in other areas of metal treatment as disclosed in U.S. Pat. Nos. 3,637,514 and 3,732,239.

For many applications, it is desirable to separate 3,4-toluenediamine from the o-toluenediamine mixture. For example, it is known that the production of 6-methyl-1,3-dithiolo (4,5-6) quinoxalin-2-one, an insecticide, acaricide and fungicide requires substantially pure 3,4-toluenediamine as a starting material.

It is thus apparent that users of 3,4-toluenediamine are frequently unable to use the mixture of o-toluenediamine isomers which results as a by-product of the overall toluene diisocyanate process described above. Accordingly, much of the mixed ortho isomer mixture is discarded, destroyed or stockpiled due to the fact that an inexpensive process has not heretofore been available to separate out the useful 3,4- isomer which generally constitutes about 50% by weight of the o-toluenediamine mixture. It is, therefore, quite apparent that a substantial portion of the costs attributable to handling, storing, shipping or discarding the o-toluenediamine mixture could be passed on to purchasers of the 3,4- isomer if an inexpensive means were available for separating the same from the o-toluenediamine mixture. Prior to the present invention, however, no such means was available.

Crystallization techniques are generally only used where it is desired to separate a pure component from a mixture containing the component and a minor amount of impurity (usually 5% of the mixture or less). Normally, however, where the impurity constitutes more than a minor amount of the mixture, one skilled in the art would not expect crystallization to be an effective tool to separate the desired component from the mixture. It would be expected that the use of crystallization techniques in such circumstances would not produce the desired degree of a separation. It was, therefore, quite surprising and unexpected to find that when an o-toluenediamine mixture containing 40 to 70% 3,4-toluenediamine and 30 to 60% 2,3-toluenediamine was dissolved in toluene and cooled, substantially pure 3,4-toluenediamine was obtained in high yields. It was also surprising in view of the structural similarity between the 2,3- and 3,4- isomers to find that crystallization could be carried out at widely varying temperatures to significantly increase yields without causing a corresponding decrease in product purity.

As used in this specification and in appended claims, all percentages are by weight unless it is stated to the contrary.

SUMMARY OF THE INVENTION

I have discovered and my invention comprises a process for separating 3,4-toluenediamine from a mixture of by-product o-toluenediamine isomers which includes 40 to 70% 3,4-toluenediamine and 30 to 60% 2,3-toluenediamine by crystallizing the 3,4- isomer from a selected solvent. The process comprises dissolving the mixture in a solvent selected from the group consisting of benzene, toluene and xylene at a selected temperature not in excess of the boiling point of the selected solvent, thereafter cooling the resulting solution to a temperature at which precipitation begins, continuing cooling until a desired amount of 3,4-toluenediamine is formed as a precipitate and recovering the 3,4-toluenediamine.

Detailed Description of the Invention

In separating 3,4-toluenediamine from a mixture of o-toluenediamine isomers a suitable starting material is the o-toluenediamine mixture obtained by distillation of reduced dinitrated toluenes. This mixture generally contains from 70 to 100% mixed o-toluenediamines, suitably 80 to 100%.

Regardless of overall ortho concentration the mix between the 3,4-o-toluenediamine and the 2,3-orthotoluenediamine isomer appears to stay relatively constant. Of the ortho isomers present in the mixture, one usually finds 40 to 70%, preferably 50 to 60% 3,4-toluenediamine and 30 to 60%, preferably 40 to 50%, 2,3-toluenediamine.

In addition, one may find various impurities present in the starting mixture depending on the precise conditions under which it was prepared. The major impurity found when a single distillation is employed is m-toluenediamine isomers, principally 2,4- and 2,6-toluenediamine. These isomers may be present in amounts ranging from 0 up to about 30% of the starting mixture. Preferably, however, the meta isomer content is limited to about 15%. Other impurities which may be present include, inter alia, nitrotoluidines, unreacted toluene and nitrotoluenes but these are generally present in minor amounts, for example, 0-2%, and have no noticeable effect on the present process.

While the present invention is primarily directed to the by-product of the above-described toluene diisocyanate process, it may also encompass separation of 3,4-toluenediamine from mixtures of o-toluene diamine isomers resulting from production of other chemicals and in fact is applicable to any mixture containing the 2,3- and 3,4-isomers in the suitable proportions described above.

In accordance with the present invention, the mixture of o-toluenediamine isomers is dissolved in a solvent selected from the group consisting of benzene, toluene and xylene. The amount of solvent necessary for the purpose of dissolving the o-toluenediamine mixture depends on the temperature at which dissolution is to be effected and/or from which crystallization is to be commenced and upon the proportions of 3,4- and 2,3- isomers in the o-toluenediamine mixture. I have found that 5 to 50 grams of the o-toluenediamine mixture may suitably be dissolved in each 100 cc of the selected solvent if a dissolution temperature not in excess of the boiling point of the solvent is employed. It is preferred, however, to employ from 10 to 40 grams of the o-toluenediamine mixture for each 100 cc of solvent and it is preferred to use toluene as the selected solvent.

As noted above, the o-toluenediamine mixture may contain certain impurities and some of these may be insoluble in the selected solvent. If such insoluble impurities are present, it is desirable that these be removed, for example by filtration, before cooling to a point at which precipitation begins to occur. In most situations, however, the by-product diamine mixture will be completely soluble and this filtration step will not be required.

The o-toluenediamine mixture may be dissolved in the selected solvent at any desired temperature. It is preferable, however, to select a temperature below the boiling point of the solvent to minimize evaporation and loss of solvent. Alternatively, of course, the dissolution and crystallization could be carried out under pressure but such procedure, while suitable, is not preferred since it merely increases the cost of the separation without providing any other advantage.

It is preferred to employ a dissolution temperature above ambient temperature if possible. By employing an elevated temperature for dissolution, necessity for forced cooling of the diamine/solvent mixture is generally avoided. While lower dissolution temperatures may be employed, no advantage is seen in utilizing the same and it is highly likely that the supplemental cooling which would be required would merely increase separation costs.

Following dissolution of the o-toluenediamine mixture in the selected solvent, the solvent is cooled or allowed to cool as the case may be to a temperature at which 3,4-toluenediamine begins to precipitate out of the solvent. In accordance with known crystallization principles, the product precipitated at this temperature is highly purified 3,4-toluenediamine. If cooling were discontinued at this point, or if the mixture were not allowed to cool below this temperature, the yield of product 3,4-toluenediamine would be somewhat limited but maximum purity would be attained. If cooling was continued or allowed to continue, yields would be improved but purity would decrease. Thus, one must strike a balance between desired yield and desired product purity.

It was quite surprising, however, to find with toluene as the solvent, one could substantially decrease temperature and thus obtain substantially increased yields and still obtain purified 3,4-toluenediamine as the product. As used herein, the term "purified" as applied to 3,4-toluenediamine means a product which exceeds about 85%, desirably 90%, 3,4-toluenediamine and preferably which exceeds 95% 3,4-toluenediamine. The relationship of purity to yield in a toluene solvent system is shown by the drawing attached hereto from which it will be observed that there was far less decrease in purity (broken line) over a temperature range of practically 30° than one skilled in the art would have expected. At the same time, there was a far greater increase in yield (solid line) than would have been expected for such a large temperature differential and small decrease in purity.

Thus, having cooled to the point at which precipitation commences, the cooling may be continued or allowed to continue to considerably lower temperatures, for example, to temperaturss in the range of −20°C. to 35°C., and yields may be substantially increased without correspondingly affecting purity of the 3,4-toluenediamine obtained. This permits one to control the inherent variables of yield and purity over a broad temperature range and thus to finely control the quantity and quality of product obtained. Thus, if crystallization commences at 35°C., the precipitate will be almost 100% 3,4-toluenediamine at 30°C. but yield will be about 20-30% of the 3,4-toluenediamine present in the starting mixture. On the other hand, if the final temperature is about −10°C., yield will be 80-90% with purity on the order of about 96% 3,4-toluenediamine.

While it is possible to continue cooling to very low temperatures, some point will be reached for each mixture and each solvent at which 2,3-toluenediamine will begin to drop out in amounts which exceed desirable limits. While this point will be dependent on the factors discussed above, it is believed to be preferable not to cool substantially below 0°C. since this, in addition to producing a less pure product, also increases energy requirements beyond what might prove to be acceptable limits.

When cooling is completed, the precipitate is separated from the mother liquor by any suitable means, for example, filtration, and dried to provide purified 3,4-toluenediamine containing at least 85%, desirably 90–100%, preferably 95–100% 3,4-toluenediamine.

EXAMPLE I 50 g of mixed o-toluenediamine containing 57% by weight 3,4-toluenediamine and 43% by weight 2,3-toluenediamine was dissolved in 250 cc of toluene. The mixture was heated to 90°C. and then cooled approximately 18 hours to 15°C. Crystallization commenced without seeding at about 35°C. The slurry was filtered with suction and pressed with a rubber dam. The cake was washed in the filter with 15 cc portion of toluene cooled to 5°C., followed by an additional 10 cc wash of toluene. The cake was pressed with the aid of a rubber dam, then blown partially dry in the filter with air. The pink solid remaining was then dried at room temperature and 1 mm Hg for 1 hour. The product was analyzed by VPC and found to contain 99.3% 3,4-toluenediamine and 0.03% 2,3-toluenediamine. The yield was 13.7 g representing a yield of 48.6% of the 3,4-toluenediamine present in the starting o-toluenediamine mixture.

EXAMPLE II

The procedure of Example I was repeated with the exception that cooling was continued to 0°C. Lowering crystallization temperature from a minimum of 15°C. to a minimum of 0°C. increased yield from 48.6% to 70%, but only decreased purity from 99.3% to 97%

What is claimed is:

1. A process for separating 3,4-toluenediamine from a mixture of 80–100% o-toluenediamine isomers of which 40-70% is 3,4-toluenediamine and 30-60% is 2,3-toluenediamine comprising: dissolving 10 to 40 grams of said mixture in each 100 cc of a solvent selected from the group consisting of benzene, toluene and xylene at a temperature not above the boiling point of the selected solvent, cooling the resulting solution to a temperature at which precipitation begins, continuing cooling until a desired amount of precipitate is formed, and separating said precipitate to provide a purified 3,4-toluenediamine.

2. The process or claim 1 in which said o-toluenediamine mixture produced by dinitrating toluene, reducing the resulting dinitrotoluenes and distilling the resulting mixture.

3. The process of claim 1 wherein said solvent is toluene.

4. The process of claim 3 wherein said mixture is dissolved in said solvent at a temperature above ambient temperature.

5. The process of claim 3 wherein said resulting solution is cooled to a temperature between ambient temperature and 0°C.

* * * * *